United States Patent [19]

Jackson et al.

[11] 3,954,745

[45] May 4, 1976

[54] PROCESS FOR PREPARING CEFAZOLIN

[75] Inventors: Billy G. Jackson; Charles W. Ryan, both of Indianapolis, Ind.

[73] Assignee: Eli Lilly and Company, Indianapolis, Ind.

[22] Filed: Sept. 12, 1974

[21] Appl. No.: 505,304

[52] U.S. Cl............................................. 260/243 C
[51] Int. Cl.² ....................................... C07D 501/06
[58] Field of Search ................................ 260/243 C

[56] References Cited
UNITED STATES PATENTS 3,502,665  3/1970  Wetherill et al. ............... 260/243 C
3,516,997  6/1970  Takano et al. .................. 260/243 C

*Primary Examiner*—Paul M. Coughlan, Jr.
*Attorney, Agent, or Firm*—William C. Martens, Jr.; Everet F. Smith

[57] ABSTRACT

Cefazolin is prepared by treating a solvate of N,N-dimethylformamide and the hydrochloride salt of 7-amino-3-(2-methyl-1,3,4-thiadiazol-5-yl)thiomethyl-3-cephem-4-carboxylic acid with 1H-tetrazole-1-acetyl chloride in the presence of N,N-dimethylacetamide as solvent.

9 Claims, No Drawings

PROCESS FOR PREPARING CEFAZOLIN

BACKGROUND OF THE INVENTION

This invention relates to a process for preparing 7-(1H-tetrazol-1-yl)acetamido-3-(2-methyl-1,3,4-thiadiazol-5-yl)thiomethyl-3-cephem-4-carboxylic acid (cefazolin).

Cefazolin is disclosed and claimed in U.S. Pat. No. 3,516,997. One of the generalized methods described in this United States patent for preparing cefazolin as well as other compounds of the therein defined genus involves reacting the corresponding 7-amino cephalosporin with an appropriate acid or reactive derivative thereof to achieve acylation of the amino function in the 7-position of the cephalosporin. The acylation reaction, the United States patent suggests, is carried out in the presence of an inert solvent, which is exemplified by acetone, dioxane, acetonitrile, chloroform, methylene chloride, ethylene chloride, tetrahydrofuran, pyridine, and the like, or a mixture of such solvents or an aqueous solution of such solvents or water or any other suitable diluent. When the cephalosporin reactant is in the form of its zwitterion, it is suggested that the reaction be effected in the presence of a base.

The acylating agent can be in its free acid form in which case the presence of a condensing agent such as N,N'-diethylcarbodiimide is employed. Alternatively, the acylating agent can be derivatized by conversion to its corresponding acid chloride, and the acid chloride can be used directly as the acylating agent. Any of the above represent generally recognized techniques for accomplishing acylation of a 7-amino cephalosporin compound.

U.S. Pat. No. 3,502,665 is directed specifically to a method for accomplishing acylation of 7-aminocephalosporanic acid (7-ACA) or derivatives of 7-ACA in which the acetoxy function in the 3-position has been displaced by other well-recognized nucleophiles. By the definition of the process of this patent, a 7-acylamidocephalosporanic acid is prepared by acylation of 7-aminocephalosporanic acid or an acid addition salt thereof by treatment with an acyl halide under substantially anhydrous conditions and in an inert Lewis base liquid which, under the conditions of the reaction, has a dielectric constant above 15 and which contains a hydrogen halide acceptor, which acceptor may itself be the Lewis base.

Included among those compounds considered as Lewis bases and mentioned for use in accordance with the process of U.S. Pat. No. 3,502,665 are certain N,N-dialkylamides. Those specifically mentioned are N,N-dimethylformamide, N,N-diethylformamide, N,N-dipropylformamide, N,N-dibutylformamide, N,N-dimethylacetamide, N,N-diethylacetamide, N,N-dimethyl valeramide, N,N-dimethylpropionamide, N-formylpiperidine, and N-formylmorpholine. It is stated that from this group it is preferred to use N,N-dimethylacetamide or N,N-dimethylformamide.

This invention is moderately related to the subject matter of the aforementioned patents and is directed to the discovery, in the preparation of cefazolin by acylation of the 7-aminocephalosporin nucleus of cefazolin, that it is highly preferred to carry out the reaction using tetrazoleacetyl chloride in the presence of N,N-dimethylacetamide as solvent. This discovery includes the finding that N,N-dimethylacetamide is highly preferred as solvent over the artrecognized, closely-related, and expected equivalent N,N-dimethylformamide.

SUMMARY OF THE INVENTION

Broadly, this invention is directed to an improvement in the process for preparing a compound of the formula

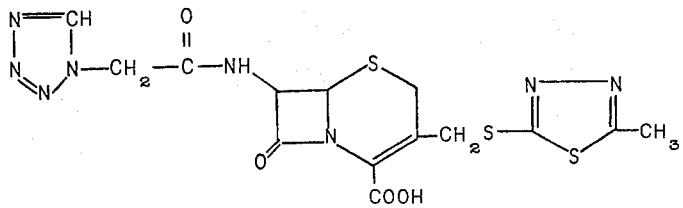

by reacting a solvate of N,N-dimethylformamide and the hydrochloride salt of a 7-aminocephalosporin compound of the formula

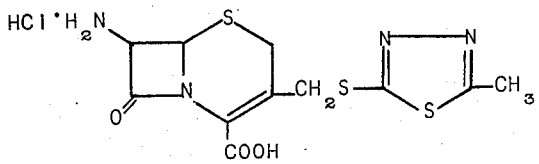

with

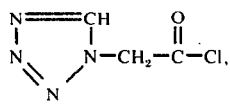

which improvement comprises carrying out the reaction in the presence of N,N-dimethylacetamide as solvent.

DETAILED DESCRIPTION OF THE INVENTION

As previously indicated, this invention is directed to the discovery that the preparation of cefazolin by acylation of a solvate of N,N-dimethylformamide in the hydrochloride salt of 7-amino-3-(2-methyl-1,3,4-thidiazol-5-yl)thiomethyl-3-cephem-4-carboxylic acid (cefazolin nucleus) using 1H-tetrazole-1-acetyl chloride can be greatly facilitated by carrying out the reaction in a solvent comprising N,N-dimethylacetamide.

The acylating agent which is employed in the process of this invention is 1H-tetrazole-1-acetyl chloride. The acid chloride acylating agent can be prepared from the corresponding 1H-tetrazole-1-acetic acid. Since the 1H-tetrazole-1-acetyl chloride product is both difficult to isolate and difficult to maintain when isolated due to its relative instability, it is preferred that the acid chloride be prepared shortly before its use.

Furthermore, in order to avoid problems which accompany isolation of the acid chloride, it is preferred also to prepare the acid chloride from its corresponding acid in an N,N-dimethylacetamide medium and then to employ the resulting reaction mixture in toto in the acylation reaction. More preferably, in preparation of the acid chloride from 1H-tetrazole-1-acetic acid, it is desirable to include a co-solvent in addition to the N,N-dimetylacetamide. Suitable co-solvents include, for example, acetonitrile, acetone, and chlorinated hydrocarbons, such as methylene chloride, chloroform, and the like. A preferred such co-solvent is acetonitrile. The presence of a co-solvent such as is described above will in no way be detrimental to the use of the resulting acid chloride reaction mixture in the subsequent acylation reaction.

The 1H-tetrazole-1-acetyl chloride can be prepared from the acid by conventional preparative techniques. These include, for example, treatment of 1H-tetrazole-1-acetic acid with phosgene, thionyl chloride, phosphorus trichloride, or phosphorus pentachloride. Preferably, however, the 1H-tetrazole-1-acetic acid is treated with phosgene. The reaction is carried out in a suitable solvent or mixture of solvents. Additional precautions may be taken to ensure that the surrounding environment is rendered inert, such as, for example, by carrying out the acid chloride preparation under an atmosphere of nitrogen.

The preferred cefazolin nucleus reactant has the following structure:

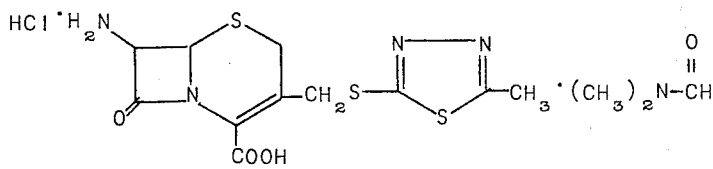

The cefazolin nucleus employed as starting material in the process of this invention is in the form of an N,N-dimethylformamide solvate of its hydrochloride salt. The solvate, as represented above, preferably comprises a 1:1 molar ratio of the hydrochloride salt nucleus and N,N-dimethylformamide.

Acylation of the solvate with the acid chloride is equimolar. Preferably, however, a slight to moderate excess, typically from about 10 percent to about 25 percent, of the acid chloride is employed since it is the more readily available of the two reactants and since the presence of such an excess will tend to cause optimum acylation of the less readily available cefazolin nucleus. Also, the presence of an excess of the acid chloride is advantageous because it will react with any moisture which may be present and thereby render the reaction medium anhydrous.

The acylation generally is carried out at a temperature of from about −10°C. to about +25°C., and preferably from about −5°C. to about +10°C. The acylation is quite rapid, generally being completed in from about 15 minutes to about 2 hours.

As indicated, the core of this invention relates to the particular solvent medium in which the acylation reaction is carried out. Specifically, the solvent medium, at least in principal composition, must be N,N-dimethylacetamide. It is not essential that N,N-dimethylacetamide be the only solvent present in the mixture. It is essential only that it be the dominant solvent in the mixture and that the other substances which are or may be present not be detrimental to the ongoing of the acylation reaction.

Thus, solvent mixtures can be employed. This is apparent from the fact that the N,N-dimethylformamide solvate of the cefazolin nucleus is employed as starting material. Inherent in the acylation of this solvate is the liberation of the N,N-dimethylformamide present therein. The thus-liberated N,N-dimethylformamide then participates in the reaction mixture as solvent, forming a solvent mixture with the already present N,N-dimethylacetamide.

Other solvents can be employed in combination with N,N-dimethylacetamide, the only requirement being that they be inert to the reactants. Typical such solvents include, for example, acetonitrile, acetone, and chlorinated hydrocarbons, such as methylene chloride, chloroform, and the like. Preferably, however, the originating solvent is comprised entirely of N,N-dimetylacetamide. By "originating solvent" is meant that substance or mixture of substances which, at the outset of the acylation process, is added specifically for the purpose of serving as solvent. By this definition, therefore, is excluded any solvent or mixture of solvents which may be present in the acylation reaction mixture by reason of the use in toto of the reaction mixture resulting from preparation of the 1H-tetrazole-1-acetyl chloride.

Other substances can likewise be present in the reaction mixture without serious detriment. For example, when the 1H-tetrazole-1-acetyl chloride reactant is prepared from the corresponding acid by treatment thereof with phosgene, the by-products which form are carbon dioxide and hydrogen chloride. As already indicated, the reaction mixture resulting from the acid chloride preparation can itself be employed in the acylation reaction. When this method is employed, the bulk of these by-products will have left the reaction mixture as gases; however, residual amount will remain and will be present in the acylation reaction mixture but will present no serious problem. Likewise, since the hydrochloride acid addition salt of the cefazolin nucleus is employed as starting material, hydrogen chloride will be freed during the acylation and thus be present in the reaction mixture, but without detriment.

It is highly preferred that the acylation reaction be carried out in an anhydrous or substantially anhydrous environment. The presence of moisture is detrimental to the 1H-tetrazole-1-acetyl chloride reactant, and, to the extent that it is present, the product yield correspondingly is diminished. Preferably, therefore, the reaction environment will be dried by any conventional technique prior to carrying out the acylation reaction.

It is also possible to employ a suitable drying agent within the reaction mixture as long as it does not hinder the acylation. For example, sufficient trimethylchlorosilane can be added to the N,N-dimetylacetamide to account for any water present in the reaction medium. This will arrest any moisture which may be present. However, care should be exercised to avoid the presence of trimethylchlorosilane in an amount in excess of that required for the moisture which is present in the system since the excess will tend to react with the cefazolin nucleus starting material.

Recovery of the 7-(1-H-tetrazol-1-yl)acetamido-3-(2-methyl-1,3,4-thiadiazol-5-yl)thiomethyl-3-cephem-4-carboxylic acid (cefazolin) can be accomplished quite simply by addition of water to the reaction mixture accompanied by reduction of the pH of the mixture to a strongly acidic range of from about 0 to about 3. Recovery can be accomplished simply by addition of water since the reaction by-product, HCl, will be present in a quantity sufficient to impart the desired pH range. The product then can be recovered by filtration from the reaction mixture.

In the event that it is desirable to separately recover any cefazolin nucleus (unacylated starting material) which may be present, this can be accomplished by maintaining the aqueous reaction mixture at a moderately acidic pH range of from about 4.5 to about 6.5. The product will remain soluble at this range whereas the cefazolin nucleus, since it is zwitterionic, will precipitate from the mixture. Since the reaction mixture containing added water will be highly acidic, the selective precipitation of any cefazolin nucleus is accomplished by raising the pH of the mixture to a level within the aforementioned range by addition, for example, of a salt of a strong base and a weak acid, preferably, an alkali metal acetate, and most preferably, sodium acetate. Upon isolation of any cefazolin nucleus, the product can be recovered by lowering the pH of the aqueous mixture to a strongly acidic range, that is, from about 0 to about 3.

The following examples are provided to illustrate this invention and to demonstrate the advantages thereof. They are not intended to be limiting upon the scope of this invention.

EXAMPLE 1

Acylation Using N,N-Dimethylformamide as Solvent

To 63 ml. of dry N,N-dimethylformamide were added under nitrogen 7.9 g. of 1H-tetrazole-1-acetic acid. The N,N-dimethylformamide was dried prior to use by distillation from calcium hydride and, upon analysis, was found to contain 0.09 percent water. The resulting solution was cooled in 2°C., and gaseous phosgene generated from 5.4 ml. of liquid phosgene was added above the solution over a 38 minute period. After addition was nearly complete, a bright yellow color developed; however, no precipitate was present.

Separately, a mixture of 0.80 ml. of trimethylchlorosilane in 63 ml. of N,N-dimethylformamide was prepared. To the mixture were added 24.0 g. of the 1:1 solvate of N,N-dimethylformamide and the hydrochloride salt of 7-amino-3-(2-methyl-1,3,4-thiadiazol-5-yl)thiomethyl-3-cephem-4-carboxylic acid. The mixture was cooled to 4°C. under nitrogen, and the prepared 1H-tetrazole-1-acetyl chloride mixture was added. The temperature of the resulting mixture rose to 5°C. and then fell to 3°C. over 30 minutes of stirring and cooling. The mixture was removed from the ice bath, and 250 ml. of water were added followed by 25.0 g. of sodium acetate. The resulting precipitate was filtered, washed with 75 ml. of water, and dried to obtain 3.75 g. of the unacylated 7-amino-3-(2-methyl-1,3,4-thiadiazol-5-yl)thiomethyl-3-cephem-4-carboxylic acid.

The filtrate was warmed to 30°C. The filtrate was acidified to pH 1.9 by addition of concentrated HCl. The resulting mixture was stirred for 15 minutes and seeded; however, no crystallization occurred. Water (15 ml.) was added to cloudiness (29°C.). The mixture was stirred for 17 minutes without crystallization occurring. Water (235 ml.) was added dropwise over a 55 minute period. An oil separated. The mixture was cooled in an ice bath and stirred for one hour. The resulting precipitate was filtered, washed with about 200 ml. of water and dried in vacuo at 50°C. to obtain 10.0 g. of 7-(1H-tetrazol-1-yl)acetamido-3-(2-methyl-1,3,4-thiadiazol-5-yl)thiomethyl-3-cephem-4-carboxylic acid.

EXAMPLE 2

Acylation Using N,N-Dimethylacetamide as Solvent

To 63 ml. of N,N-dimethylacetamide were added under nitrogen atmosphere 7.9 g. of 1H-tetrazole-1-acetic acid. The resulting mixture was cooled in an ice bath. To the stirred solution gaseous phosgene generated from 5.3 ml. of liquid phosgene was added above the solution over a period of 30 minutes. The temperature of the mixture rose to 10°C., and then dropped to 7°C.

A separate mixture of 0.62 ml. of trimethylchlorosilane in 63 ml. of N,N-dimethylacetamide was prepared and cooled under nitrogen in an ice bath. To the mixture were added 24.0 g. of the 1:1 solvate of N,N-dimethyformamide and the hydrochloride salt of 7-amino-3-(2-methyl-1,3,4-thiadiazol-5-yl)thiomethyl-3-cephem-4-carboxylic acid. To the resulting mixture was then added the previously prepared 1H-tetrazole-1-acetyl chloride reaction mixture. The temperature of the resulting stirred and cooled mixture rose to 12°C. and after 5 minutes fell to 4°C. Stirring was continued for an additional 25 minutes. Cooling was discontinued, and 250 ml. of water were added followed by 25 g. of sodium acetate. The mixture was stirred to dissolve the sodium acetate, the pH of the resulting mixture being 4.6. A slight precipitate formed, was filtered, and washed with 25 ml. of water. The solid was dried to obtain 0.105 g. of the unacylated 7-amino-3-(2-methyl-1,3,4-thiadiazol-5-yl)thiomethyl-3-cephem-4-carboxylic acid.

The filtrate was warmed to 30°C. and acidified to pH 1.9 by addition of concentrated HCl. The mixture was seeded and allowed to stand. After 20 minutes crystals began to form. The mixture was stirred for 35 minutes at 28°–31°C. Water (250 ml.) was added dropwise over a 25 minute period. The mixture was cooled in an ice bath and stirred for 1 hour at 5°C. or less. The resulting precipitate was filtered, washed with about 300 ml. of water, and dried in vacuo at 50°C. to obtain 21.2 g. of 7-(1H-tetrazol-1-yl)acetamido-3-(2-methyl-1,3,4-thiadiazol-5-yl)thiomethyl-3-cephem-4-carboxylic acid.

EXAMPLE 3

Acylation Using a Mixture of Solvents

To a mixture of 40 ml. of acetonitrile and 5.4 ml. of N,N-dimethylacetamide were added under nitrogen 7.5 g. of 1H-tetrazole-1-acetic acid. The resulting mixture was cooled to about 2°C. in an ice bath. To the stirred solution gaseous phosgene generated from 5.0 ml. of liquid phosgene was added above the solution over a period of 28 minutes. The resulting mixture was stirred for four minutes, and 25 ml. of N,N-dimethylacetamide were added over a period of 10 minutes.

A separate mixture of 1.34 ml. of trimethylchlorosilane and 24.0 g. of the 1:1 solvate of N,N-dimethylformamide and the hydrochloride salt of 7-amino-3-(2-methyl-1,3,4-thiadiazol-5-yl)thiomethyl-3-cephem-4-carboxylic acid in 63 ml. of N,N-dimethylacetamide was prepared and cooled under nitrogen in an ice bath. To the resulting mixture maintained at 1°C. then was added the previously prepared 1H-tetrazole-1-acetyl-chloride reaction mixture. The temperature of the resulting mixture rose upon addition of the acid chloride mixture from 1° to 11.5°C. The resulting mixture was stirred under nitrogen with ice bath cooling for 30 minutes. Cooling was discontinued, and 170 ml. of water were added, the temperature of the mixture rising to 26°C. The mixture was seeded with product obtained from a previous preparation. Crystals formed within 1 minute. The resulting mixture was stirred for 10 minutes, and 350 ml. of water were added over a period of 33 minutes. The mixture then was cooled in an ice bath to below 5°C. and was stirred with cooling for 1.5 hours. The precipitate was filtered, washed with water, and dried in vacuo at room temperature to obtain 21.5 g. of 7-(1H-tetrazol-1-yl)acetamido-3-(2-methyl-1,3,4-thiadiazol-5-yl)thiomethyl-3-cephem-4-carboxylic acid.

We claim:

1. In a process for the preparation of a compound of the formula

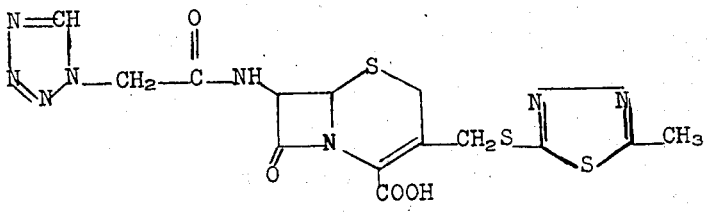

by reacting a solvate of N,N-dimethylformamide and the hydrochloride salt of a 7-aminocephalosporin compound of the formula

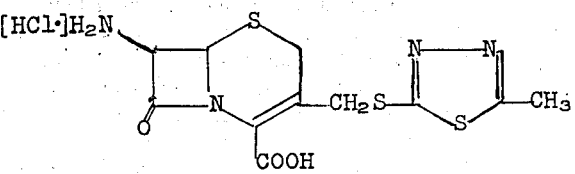

with 1H-tetrazole-1-acetyl chloride of the formula

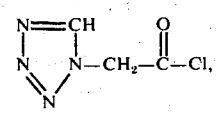

the improvement which comprises carrying out the reaction in the presence of an originating solvent comprising N,N-dimethylacetamide.

2. Process of claim 1, in which the originating solvent consists of N,N-dimethylacetamide.

3. Process of claim 1, in which the source of the 1H-tetrazole-1-acetyl chloride is a reaction mixture resulting from reaction of 1H-tetrazole-1-acetic acid with phosgene.

4. Process of claim 3, in which the reaction mixture resulting from the preparation of 1H-tetrazole-1-acetyl chloride contains a mixture of N,N-dimethylacetamide and an inert solvent.

5. Process of claim 4, in which the inert solvent is acetonitrile.

6. Process of claim 1, in which the reaction is carried out in a substantially anhydrous environment.

7. Process of claim 6, in which the reaction is carried out at a temperature of from about −10°C. to about 35°C.

8. Process of claim 7, in which the reaction is carried out at a temperature of from about 0°C. to about 10°C.

9. Process of claim 1, in which the solvate comprises a 1:1 molar ratio of the hydrochloride salt of the 7-aminocephalosporin and N,N-dimethylformamide.

* * * * *